(12) United States Patent
Kimura et al.

(10) Patent No.: US 7,057,157 B2
(45) Date of Patent: Jun. 6, 2006

(54) PHOTOSENSOR DEVICE AND DISK INSPECTION APPARATUS USING IT

(75) Inventors: Hayato Kimura, Machida (JP); Toshimi Nagaishi, Machida (JP); Haruhiko Tsuchiya, Machida (JP)

(73) Assignee: Kirin Techno-System Corporation, Yokohama (JP)

( * ) Notice: Subject to any disclaimer, the term of this patent is extended or adjusted under 35 U.S.C. 154(b) by 0 days.

(21) Appl. No.: 10/005,532

(22) Filed: Oct. 29, 2001

(65) Prior Publication Data
US 2002/0079434 A1    Jun. 27, 2002

(30) Foreign Application Priority Data

| Nov. 2, 2000 | (JP) | ............................. 2000-335786 |
| Nov. 2, 2000 | (JP) | ............................. 2000-335881 |

(51) Int. Cl.
*G01J 1/04*        (2006.01)
(52) U.S. Cl. ............................. 250/227.11; 250/559.01
(58) Field of Classification Search ............ 356/237.1, 356/239.3, 239.7, 239.8, 237.2, 237.3; 250/227.11, 250/227.14, 227.18, 227.26, 227.28, 227.29, 250/559.04–559.08, 559.41, 559.44, 559.45, 250/227.2, 201.5, 216, 559.01, 559.03
See application file for complete search history.

(56) References Cited

U.S. PATENT DOCUMENTS 4,809,188 A  *  2/1989  Willits et al. ............... 700/125
5,308,993 A      5/1994  Holman et al.
5,483,347 A  *  1/1996  Hollmann ................... 356/624
5,898,499 A  *  4/1999  Pressesky ................... 356/511
5,914,495 A      6/1999  Ishizuka et al.
5,964,391 A  * 10/1999  Cain et al. .................... 226/45
5,966,212 A  * 10/1999  Hendler et al. .......... 356/239.3
6,011,618 A      1/2000  Iwata et al.
6,445,447 B1 *  9/2002  Wang et al. ............. 356/237.2

FOREIGN PATENT DOCUMENTS

| JP | 64-054304 A | 1/1989 |
| JP | 08-334471   | * 12/1996 |
| JP | 08-334471 A | 12/1996 |
| JP | 2000-171405 | 6/2000 |

* cited by examiner

*Primary Examiner*—David V. Bruce
*Assistant Examiner*—Hoon Song
(74) *Attorney, Agent, or Firm*—Frishauf, Holtz, Goodman & Chick, P.C.

(57) ABSTRACT

A photosensor device is provided which includes a light-applying fiber to apply an inspection light to a subject to be inspected; a light-receiving fiber to receive a reflected light from the subject to be inspected; a laser beam source to emit the inspection light to the light-applying fiber; and a photosensor to receive the reflected light via the light-receiving fiber. A disk inspection apparatus for inspecting surface conditions of a disk is also provided which includes a turning table for rotating the disk; a photosensor body disposed opposite to the surface of the disk; and a transfer mechanism for reciprocally transferring the photosensor body in a direction perpendicular to a rotating direction of the disk along the surface of the disk; wherein the photosensor device is utilized as the photosensor body.

1 Claim, 10 Drawing Sheets

PHOTOSENSOR DEVICE AND DISK INSPECTION APPARATUS USING IT

FIELD OF THE INVENTION

The present invention relates to a photosensor device which detects fine scratches, distortion or the like on the surface of a subject to be inspected, and a disk inspection apparatus using it to inspect defects of disks.

BACKGROUND OF THE INVENTION

In general, when the presence or absence of scratches, pinholes, distortion or the like formed on the surface of a subject to be inspected is inspected with a photosensor device of such a type, a casing of this device is disposed opposite to the surface of the subject to be inspected at a predetermined distance, inspection light is applied to the subject to be inspected from a light-applying fiber installed in this casing, and reflected light from the subject to be inspected is received by a photosensor through a light-receiving fiber.

The reflected light received by the photosensor is photo-electrically converted and output to an arithmetic section, and it is judged whether or not the voltage value (received light intensity) is within a certain set value. At that time, when scratches, pinholes, distortion or the like exist on the surface of the subject to be inspected, the reflected light is scattered or deflected, whereby the received light intensity detected by the photosensor decreases. As a result, when the received light intensity (voltage value) detected by the photosensor is less than a certain set level, an inspector may judge that scratches or the like exist on the surface of the subject to be inspected.

Incidentally, in many cases, the light-applying fiber installed in the casing is extended from this casing and connected to a light source device prepared at the outside, and inspection light emitted from a light source such as a semiconductor laser installed in the light source device is applied to the subject to be inspected via the light-applying fiber.

When the distance between the photosensor and the light source device is relatively long, it is demanded to sufficiently guarantee the strength and durability, whereby the cost becomes high. Further, the optical fiber connecting them has a flexibility and is thus likely to tremble, and when the optical fiber trembles, noise is likely to be made and properties of the inspection light tend to change, such being inconvenient.

Further, a connector portion which connects the optical fiber and the light source device is likely to be overloaded, and therefore it is also demanded to sufficiently guarantee the durability of this connector portion.

On the other hand, in general, optical disks such as CD (compact disk) are prepared by forming a recording film by coating on the surface of a polycarbonate resin substrate, and further providing a reflecting film on its surface. If defects such as scratches exist on the reflecting film or the like, recording properties will be remarkably impaired. Accordingly, various inspection devices to detect the defects have been proposed.

For example, JP-A-2000-171405 discloses a disk inspection apparatus in which a laser beam is irradiated on a rotating magnetic recording disk, and reflected light is received by a CCD array, and luminance data of each received pixel is compared with a preliminarily set luminance threshold to judge the presence or absence of defects on the disk surface.

However, in the disk inspection apparatus disclosed in the above publication, an expensive CCD array is used as an element to receive the reflected light from the disk, and further a means for image processing by each pixel the results obtained from the light received by the CCD array, whereby the structure is complicated and the unit cost of product is high. Accordingly, provision of the disk inspection apparatus of this type in a plural number in production steps leads to rise of the cost for equipment and is therefore unlikely to be realized.

As a result, since the disk inspection apparatus is used for inspection of finished disks only, even if defects are formed during the production steps, the defects will not be found until completion of production, whereby the yield of products is low, such being problematic.

SUMMARY OF THE INVENTION

Accordingly, it is the first object of the present invention to provide at a low cost a photosensor device excellent in the durability without changing the properties of the inspection light. Further, the second object of the present invention in to provide a disk inspection apparatus by which the unit cost of apparatus is low by using the above photosensor device; the cost of equipment is not so much increased even if the photosensor device is provided in a plural number in the production steps; and by providing the photosensor device in a plural number in the production steps, defects formed during the production can be instantly defected, whereby the yield of products can be improved.

In order to accomplish the above objects, the present invention provides a photosensor device, which comprises a light-applying fiber to apply an inspection light to a subject to be inspected; a light-receiving fiber to receive a reflected light from the subject to be inspected; a laser beam source to emit the inspection light to the light-applying fiber; a photosensor to receive the reflected light via the light-receiving fiber; and a casing enclosing the light-applying fiber, the light-receiving fiber, the laser beam source and the photosensor.

According to the photosensor device of the present invention, since the light-applying fiber, light-receiving fiber, laser beam source and photosensor are enclosed in one casing, connection with external units with a fiber cable is no longer required, and the durability and reliability can be improved.

In the photosensor device of the present invention, it is preferred to prepare a sensor unit as one channel which comprises the light-applying fiber, the light-receiving fiber which forms a pair with the light-applying fiber, the laser beam source connected to the light-applying fiber, and the photosensor connected to the light-receiving fiber; and dispose such sensor units as multi-channels in the casing to produce a fiber array. By such a structure, it is possible to inspect a wide inspection area in a short period of time.

The present invention also provides a disk inspection apparatus for irradiating an inspection light on a surface of a rotating disk and inspecting surface conditions of the disk based on a reflected light, which comprises a turning table for rotating the disk fitted thereon; a photosensor body disposed opposite to the surface of the disk; and a transfer means for reciprocally transferring the photosensor body in a direction perpendicular to a rotating direction of the disk along the surface of the disk; wherein the photosensor body comprises a fiber array constructed by arranging sensor units as multi-channels, each of the sensor units comprising as one unit, a light-applying fiber, a light-receiving fiber which forms a pair with the light-applying fiber, a laser beam source connected to the light-applying fiber, and a photosensor connected to the light-receiving fiber.

According to the disk inspection apparatus of the present invention, when a disk is fitted in the turning table and rotated, the photosensor body disposed opposite to the surface of the disk is transferred by a transfer means in a direction perpendicular to a rotating direction of the disk, and at this time, the inspection light is irradiated onto the surface of the disk from the light-applying fiber of fiber bundles which constitute the fiber array provided in the photosensor body, the reflected light is received by the photosensor via the light-receiving fiber of the fiber bundles, and the presence or absence of defects on the disk surface is detected based on the quantity of the reflected light received by the photosensor. And, the fiber array is composed of plural fiber bundles, and the inspection of defects on the disk surface is made while transferring the photosensor body in a direction substantially perpendicular to the rotating direction of the disk, whereby the entire surface of the disk can be inspected without arranging the fiber bundled densely.

In the disk inspection apparatus of the present invention, it is preferred to arrange the fiber arrays in plural lines in such a state that the phases of adjacent fiber arrays are shifted. By this structure, the fiber bundles can be arranged as dense as possible along the direction perpendicular to the direction for inspection.

DESCRIPTION OF THE PREFERRED EMBODIMENTS

Figure 1:
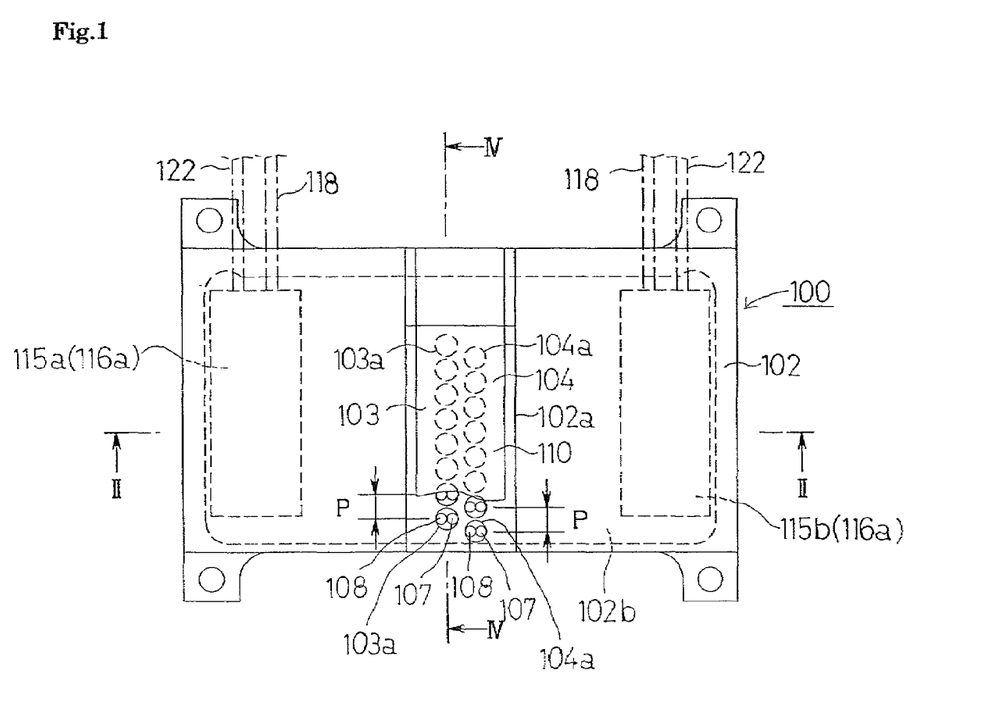
FIG. 1 is a plane view showing a state of the first embodiment of a photosensor device.
Figure 2:
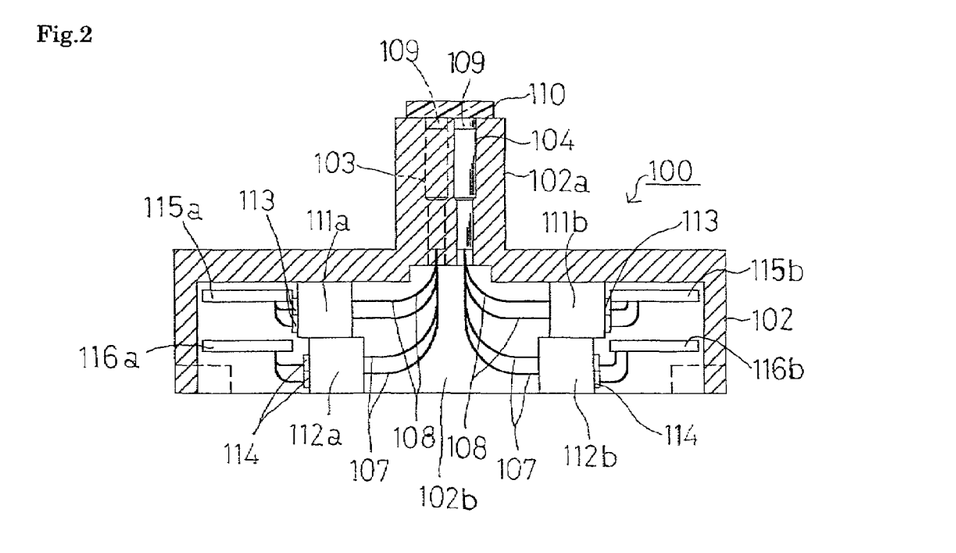
FIG. 2 is a sectional view along line II—II in FIG. 1.
Figure 3:
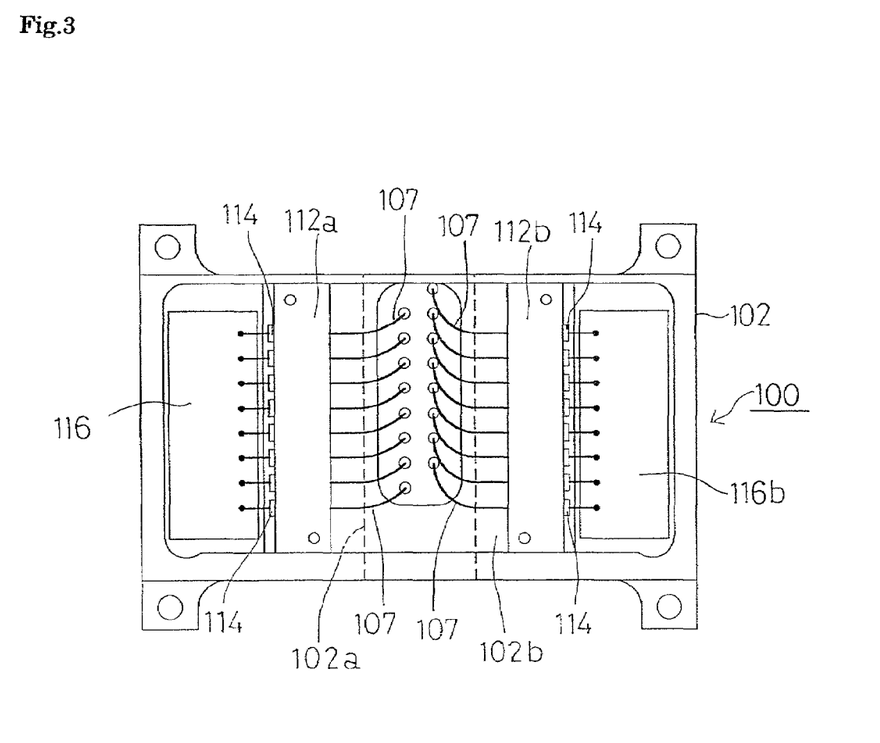
FIG. 3 is a bottom view of the photosensor device.
Figure 4:
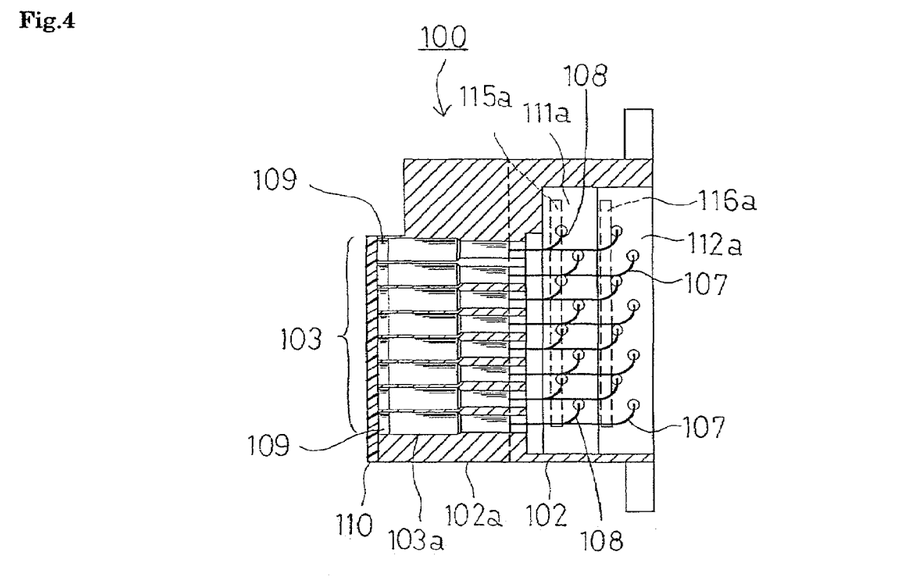
FIG. 4 is a sectional view along line IV—IV in FIG. 1.
Figure 5:
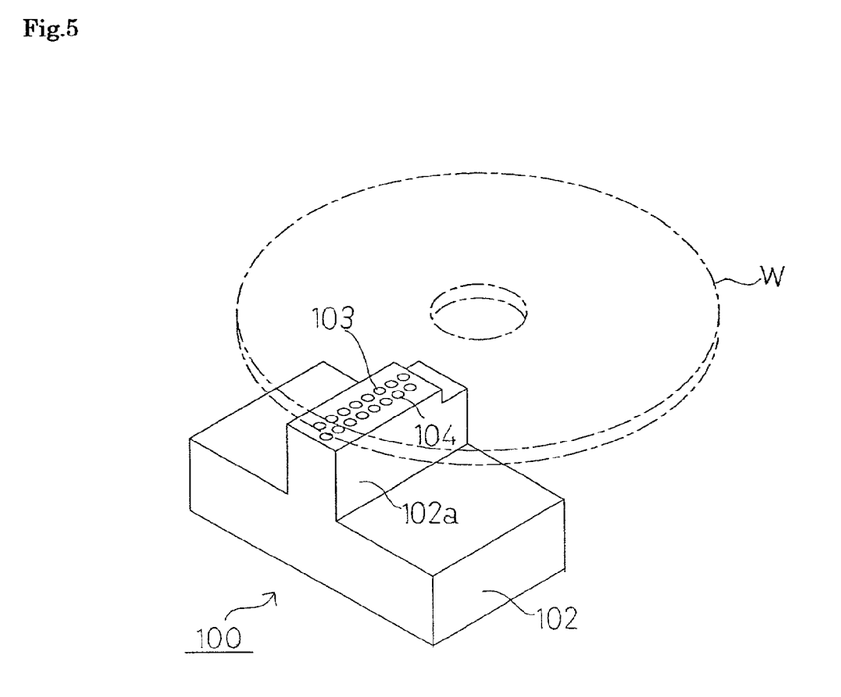
FIG. 5 is a perspective view of the photosensor device.
Figure 6:
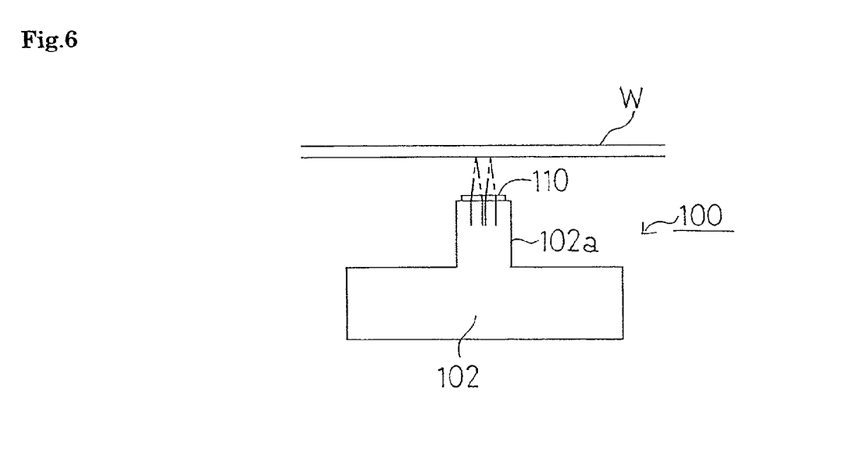
FIG. 6 is a schematic side view of the photosensor device.
Figure 7:
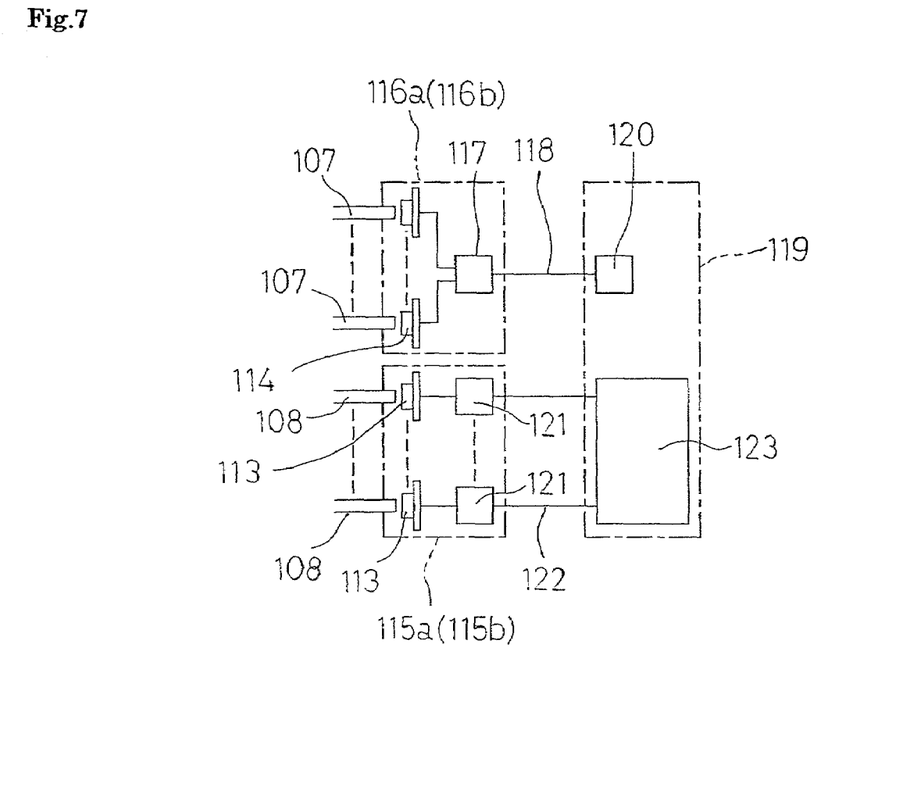
FIG. 7 is a circuit diagram of the photosensor device.

FIGS. 1 to 7 show the first embodiment of the photosensor device of the present invention. FIG. 1 is a plane view of the photosensor device. FIG. 2 is a sectional view along line II—II in FIG. 1. FIG. 3 is a bottom view of the photosensor device. FIG. 4 is a sectional view along line IV—IV in FIG. 1. FIG. 5 is a perspective view of the photosensor device. FIG. 6 is a schematic side view of the photosensor device. FIG. 7 is a circuit diagram of the photosensor device.

In these drawings, numeral 100 denotes a photosensor device. A front end portion for inspection 102a extends from the center of the upper face of a casing 102 of the photosensor device 100. At the front end portion for inspection 102a, two lines of fiber arrays 103, 104 are arranged. In this embodiment, the fiber arrays 103, 104 are constituted by 8 channels of fiber bundles 103a, 104a, respectively. The fiber bundles 103a, 104a in respective lines are arranged with a predetermined pitch P, and the fiber bundles 103a, 104a adjacent to each other arranged in such a state that the phase of either one is shifted by a half pitch to another one.

Each of the fiber bundles 103a, 104a is constructed by bundling a light-applying fiber 107 and a light-receiving fiber 108. An objective optical system 109 is provided at the front end of each of the fiber bundles 103a, 104a, and the objective optical system 109 is exposed on a front end face of the front end portion for inspection 102a. Further, at the front end face of the front end portion for inspection 102a, a transparent protecting cover 110 made of glass or the like is fixed.

As shown in FIG. 2, in the casing 102, a housing of circuit parts 102b having an opening at the bottom is formed. At both sides of the front end portion for inspection 102a of the housing of the circuit parts 102b, holding members at the light-receiving side 111a, 111b and holding members at the light-applying side 112a, 112b are arranged in upper and lower two stages in such a state that respective ones are arranged opposite to one another.

On each of the front faces of the holding members at the light-receiving side 111a, 111b, which are facing each other, a rear end of a strand in the light-receiving fiber 108 of each of the fiber bundles 103a, 104a is held via a ferule (not shown). Further, to each of back faces of the holding members at the light-receiving side 111a, 111b, a photosensor 113 corresponding to each light-receiving fiber 108 is fixed. The light-receiving face of each photosensor 113 has a continuity with each light-receiving fiber 108 via the ferule (not shown).

On the other hand, on each of the holding members at the light-applying side 112a, 112b, a rear end of a strand in the light-applying fiber 107 of each of the fiber bundles 103a, 104a is held via a ferule (not shown). Further, to each of side faces of the holding members at the light-applying side 112a, 112b, which are facing the light-applying fiber 107, a semiconductor laser generator 114 as a laser beam source is fixed. The light-applying face of each semiconductor laser generator 114 has a continuity with each light-applying fiber 107 via the ferule (not shown).

Further, circuit boards at the light-receiving side 115a, 115b are provided at the back faces of the holding members at the light-receiving side 111a, 111b, and circuit boards at the light-applying side 116a, 116b are provided at the holding members at the light-applying side 112a, 112b.

As shown in FIG. 7, on each of the circuit boards at the light-applying side 116a, 116b, a semiconductor laser generator 114 is mounted and at the same time, a head amplifier 117 of a predetermined input impedance for supplying a voltage to each semiconductor laser generator 114 is provided. This head amplifier 117 is connected to a constant voltage circuit 120 provided in an external unit 119 via an external connection cable 118.

In addition, on each of the circuit boards at the light-receiving side 115a, 115b, a photosensor 113 is mounted and at the same time, an amplifying circuit 121 for amplifying the voltage photoelectrically converted with the photosensor 113 is provided. This amplifying circuit 121 is connected to an arithmetic circuit 123 provided in the external unit 119 via a signal cable for external connection 122. An opening portion of the housing of circuit parts 102*b* is closed with a cover not shown.

Moreover, numeral W in FIGS. 5 and 6 denotes a subject to be inspected W in a disk shape, for example, CD (compact disk), DVD (digital versatile disk) or HD (hard disk). The photosensor device 100 is provided in an inspection step of a production line for the subject to be inspected W. An inspection light is applied or irradiated over the surface of the subject to be inspected W from the light-applying fiber 107, the reflected light is received by the photosensor 113 via the light-receiving fiber 108, and the presence or absence of scratches, pinholes or distortion on the surface of the subject to be inspected W is inspected based on the received light intensity.

Then, explanation will be made about the operation of this embodiment having the above structure. When a driving voltage is transmitted from the constant voltage circuit 120 provided in the external unit 119 to the photosensor device 100 via the external connection cable 118, the driving voltage is supplied to respective semiconductor laser generators 114 from the head amplifier 117 mounted on the circuit boards at the light-applying side 116*a*, 116*b* which are provided in the casing of the photosensor device 100, and then the inspection light is emitted from the semiconductor laser generators 114. The inspection light is introduced into the light-applying fiber 107, and focused in a predetermined manner with an objective optical system 109 and irradiated on the surface of the subject to be inspected W.

Then, the reflected light from the surface of the subject to be inspected W is introduced into the light-receiving fiber 108 via the objective optical system 109, and received by the photosensor 113. The quantity of the reflected light is photoelectrically converted, and then amplified in a predetermined manner with the amplifying circuit 121, and output to the arithmetic circuit 123 provided in the external unit 119 via the signal cable for external connection 122.

When scratches, pinholes, distortion or the like is formed on the surface of the subject to be inspected W, since the reflected light is scattered, the quantity of the reflected light to be received by the photosensor 113 is reduced, and the voltage output from the amplifying circuit 121 is also reduced.

In the arithmetic circuit 123, based on the voltage value output from the amplifying circuit 121, presence or absence of scratches, pinholes or distortion on the surface of the subject to be inspected W is inspected.

For example, when the fiber arrays 103, 104 are provided in two lines and the length thereof in the direction of lines is equal to the radius of the recording face provided on the disk-like subject to be inspected W, the presence or absence of scratches or the like on the entire surface of the rotating disk-like subject to be inspected W can be inspected, by moving the photosensor device 100 at a predetermined speed in a direction of the lines of the fiber arrays 103, 104 by ½ of the pitch P of respective fiber bundles 103*a*, 104*a* constituting the fiber arrays 103, 104.

Incidentally, respective fiber arrays 103, 104 may be constituted by 9 channels or larger, or 7 channels or smaller, otherwise the fiber arrays may be arranged in three or more lines with the pitch shifted. Further, respective fiber arrays may be radially arranged.

According to this embodiment, since the semiconductor laser generator 114 and the photosensor 113 are enclosed in the casing 102 of the photosensor device 100, the photosensor device 100 may be connected to the external unit 119 only with the external connection cable 118 for voltage supply to supply the driving voltage to the semiconductor laser generator 114 and the signal cable for external connection which transmits the electric signal photoelectrically converted by the photosensor 113, whereby the connection operation can be made easily.

Further, since it is no longer required to connect the casing 102 and the external unit 119 with a fiber cable, the entire system can be simplified and low production cost can be realized. Further, since the external connection cable is made of only an electric cable, the durability of the external connection cable can be improved and the reliability of product can be improved.

Moreover, since the semiconductor laser generator 114 is enclosed in the casing 102, not only the length of the light-applying fiber 107 which introduces the inspection light from the semiconductor laser generator 114 into the direction of light application, can be remarkably shortened, but also the light-applying fiber 107 can be secured inside the casing 102, whereby stable inspection light properties without incorporation of noise can be obtained.

The housing of circuit parts 102*b* of the casing 102 may be encapsulated with, if necessary, fillers such as grease, resins, powder which hardly impart a pressing force to the light-applying fiber 107 and the light-receiving fiber 108, so as to improve the vibration resistance.

Figure 8:
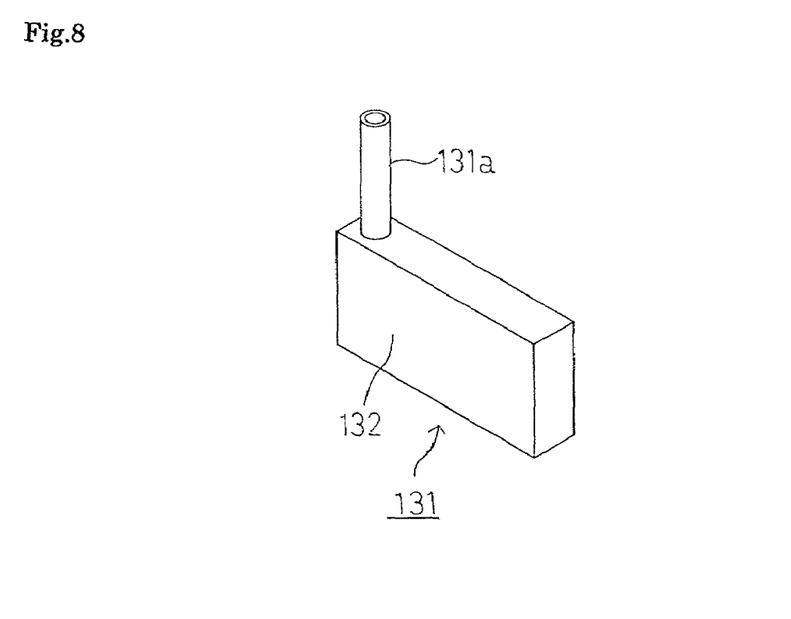
FIG. 8 is a perspective view showing the second embodiment of the photosensor device.

Next, a perspective view of a photosensor device according to the second embodiment of the present invention is shown in FIG. 8. In the above first embodiment, two lines of the fiber arrays 103, 104 are provided in the photosensor device 100. In a photosensor device 131 according to the second embodiment, a fiber bundle made of one light-applying fiber 107 and one light-receiving fiber 108 (reference can be made to FIG. 1) is provided at the front end portion for inspection 131*a* of a cylindrical shape.

Inside a casing 132 of the photosensor device 131, a substrate (not shown) on which a semiconductor laser generator and a photosensor are mounted, is enclosed, and the semiconductor laser generator and the light-applying fiber, and the photosensor and the light-receiving fiber are connected with ferules.

According to this structure, since the semiconductor laser generator and the photosensor are enclosed in a casing 132, it is no longer required to connect the casing 132 and an external unit with a fiber cable like in the first embodiment, whereby the entire system can be simplified and low production cost can be realized. In addition, the durability of the external connection cable can be improved and the reliability of product can be improved.

In this instance, the fiber array may be constructed by combining a plurality of photosensor devices 131.

Figure 9:
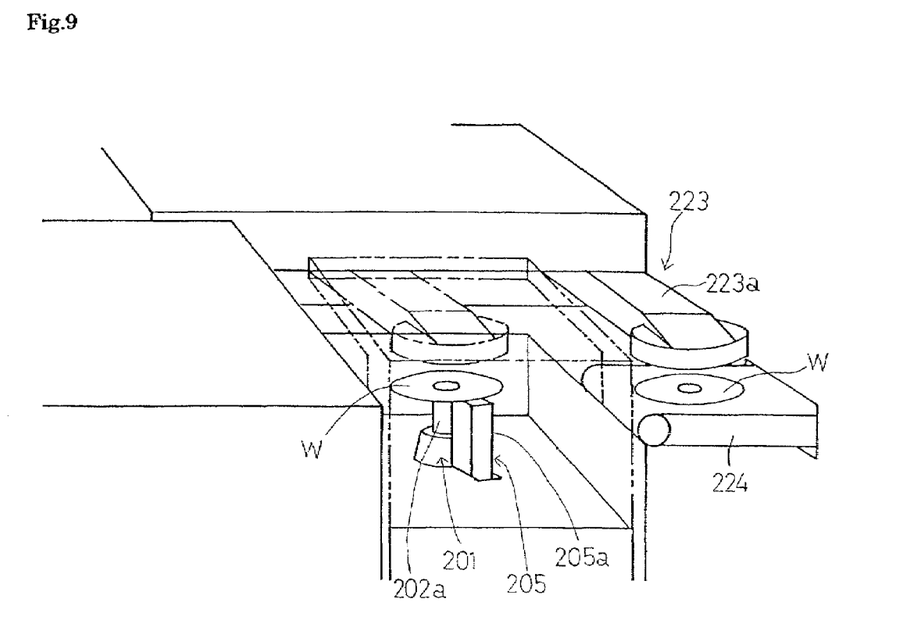
FIG. 9 is a perspective view showing the first embodiment of the disk inspection apparatus which is a handler unit having the disk inspection apparatus incorporated therein.
Figure 10:
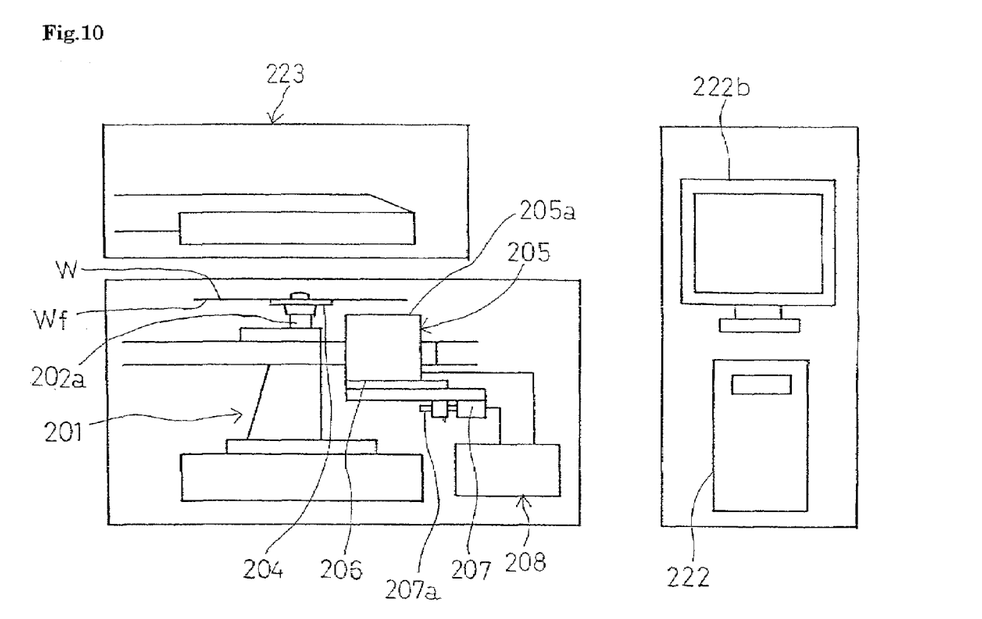
FIG. 10 is a view showing the system structure of the disk inspection apparatus.
Figure 11:
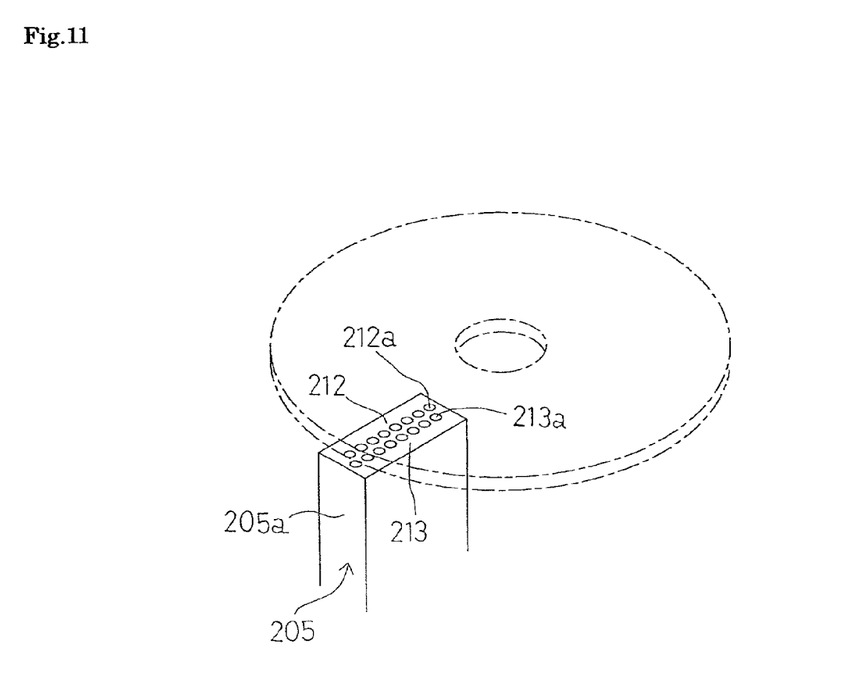
FIG. 11 is a perspective view showing a photosensor body to be used for the disk inspection apparatus.
Figure 12:
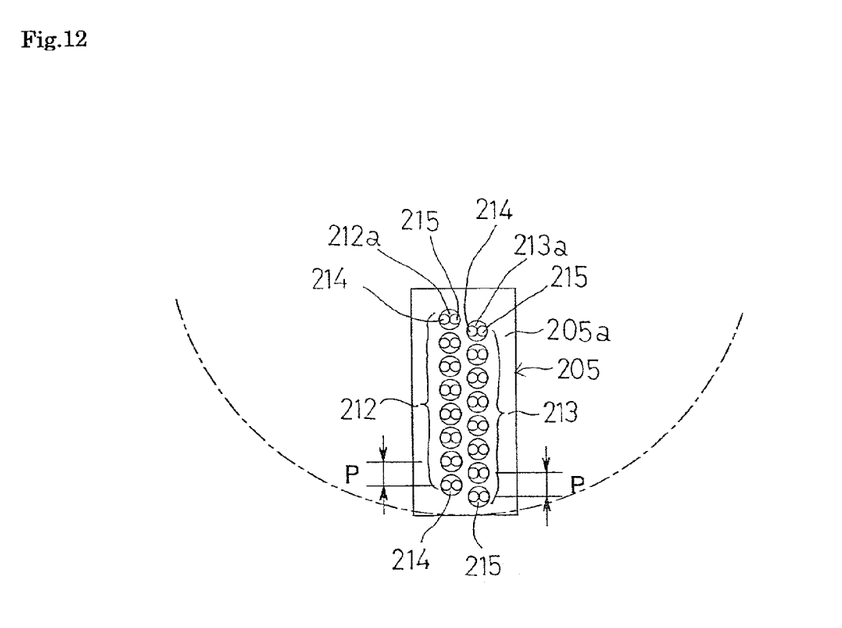
FIG. 12 is a plane view of the photosensor body.
Figure 13:
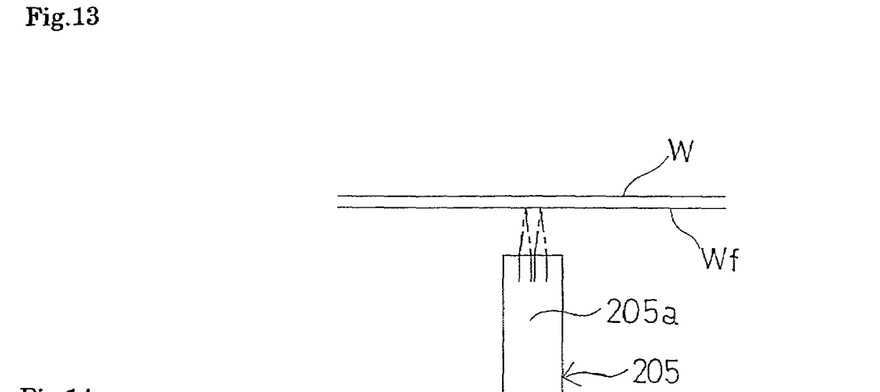
FIG. 13 is a schematic side view of the photosensor body.
Figure 14:
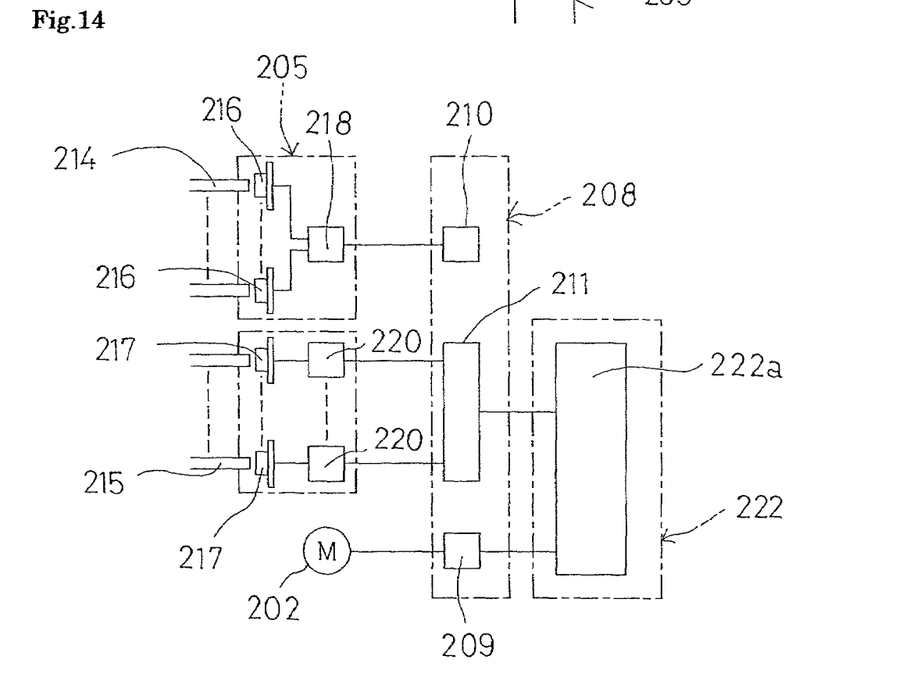
FIG. 14 is a circuit diagram of the photosensor body.

Next, FIGS. 9 to 16 show the first embodiment of the disk inspection apparatus of the present invention utilizing the above-mentioned photosensor device. FIG. 9 is a perspective view of a handler unit having the disk inspection apparatus incorporated therein. FIG. 10 is a view of the system structure of the disk inspection apparatus. FIG. 11 is a perspective view of a photosensor body. FIG. 12 is a plane view of the photosensor body. FIG. 13 is a schematic side view of the photosensor body. FIG. 14 is a circuit diagram of the photosensor body.

Numeral 201 in FIGS. 9 and 10 denotes a rotary driving portion of the disk inspection apparatus. At the front end portion of a spindle 202a protruding from a built-in motor 202 (reference can be made to FIG. 14), a rotary table 204 is provided. On this rotary table 204, a disk W such as a finished or semi-finished CD (compact disk) is mounted.

Further, on the surface Wf of the disk W to be mounted on the rotary table 204 (the underside surface of the disk in the drawings), a front end portion for inspection 205a of a photosensor body 205 is provided opposite to the surface Wf with a predetermined distance. The photosensor body 205 is mounted on and fixed to a slide table 206. To the slide table 206, is connected a ball screw 207a of a slide motor 207 which is a transferring means for reciprocatively moving the slide table 206 in a direction substantially perpendicular to the rotation direction of the disk W, along the surface Wf of the disk W. This slide motor 207 is connected to a driving unit 208.

As shown in FIG. 14, the driving unit 208 is provided with a motor control portion 209 which outputs a driving signal to the slide motor 207, a constant voltage circuit 210 which supplies a constant voltage to the photosensor body 205, and an A/D converter 211 which converts an analog signal from the photosensor body 205 to a digital signal.

On the other hand, on the front end portion for inspection 205a of the photosensor body 205, fiber arrays 212, 213 are arranged in two lines. These fiber arrays 212, 213 are constituted by fiber bundles 212a, 213a each having 8 channels. Respective fiber bundles 212a, 213a are arranged with a predetermined pitch P in such a state that a fiber bundle 212a and an adjacent fiber bundle 213a are arranged with a phase shifted by a half pitch.

Each of the fiber bundles 212a, 213a is constituted by a light-applying fiber 214 and a light-receiving fiber 215 which are bundled. At the front end portion of each of the fiber bundles 212a, 213a, an objective optical system (not shown) is provided.

Further, as shown in FIG. 14, at the rear end of the light-applying fiber 214 of each of the fiber bundles 212a, 213a, a laser beam source 216 such as a semiconductor laser generator is provided opposite to the rear end. In addition, a photosensor 217 is provided opposite to the rear end of the light-receiving fiber 215. The light-applying fiber 214 and the laser beam source 216, and the light-receiving fiber 215 and the photosensor 217, are connected via ferules (not shown).

Each laser beam source 216 is connected to a head amplifier 218 of a predetermined input impedance provided in the photosensor body 205, and this head amplifier 218 is connected to the constant voltage circuit 210 provided in the driving unit 208.

Further, each photosensor 217 is connected to an amplifying circuit 220, and this amplifying circuit 220 is connected to the A/D converter provided in the driving unit 208.

Moreover, as shown in FIGS. 10 and 14, the driving unit 208 is connected to a control unit 222a of a host computer 222. Here, numeral 222b denotes a monitor. In the control unit 222a, based on the output signal from the photosensor 217 provided in the photosensor body 205, the presence or absence of scratches, pinholes or distortion on the surface Wf of the disk W is inspected.

Further, as shown in FIG. 9, the rotary table 204 is incorporated in a handler unit 223 which is interposed in the line for transferring the disk W. The handler unit 223 has a handler 223a which sucks the disk W conveyed from a transport line 224 at the upstream side and places the disk W on the rotary table 204, and also sucks the disk W mounted on the rotary table 204 and transfers it to a transport line at the downstream side (not shown). Here, the handler unit 223 is controlled and operated based on the signals from the control unit 222a.

Next, the operation of the embodiment of the above structure will be explained. When the disk W is conveyed from the transport line 224 at the upstream side, the handler 223a of the handler unit 223 moves synchronistically, and sucks the disk W, and then put the disk W on the rotary table 204 of the disk inspection apparatus.

Whereupon, the rotary table 204 rotates, and then the slide motor 207 connected via a ball screw 207a to the slide table 206 on which the photosensor body 205 is mounted opposite to the surface Wf of the disk W, rotates, thereby moving the photosensor body 205 at a predetermined speed in a direction substantially perpendicular to the rotation direction of the disk W.

On the other hand, a driving voltage is supplied from the constant voltage circuit 210 provided in the driving unit 208 of the disk inspection apparatus to each laser beam source 216 via the head amplifier 218, whereby an inspection light is emitted from the laser beam source 216.

The inspection light is introduced into the light-applying fiber 214 of each of the fiber bundles 212a, 213a constituting the fiber arrays 212, 213 provided at the front end portion for inspection 205a of the photosensor 205, and focused in a predetermined manner with an objective optical system (not shown), and irradiated on the surface Wf of the disk W.

Then, the light reflected from the surface Wf of the disk W is introduced into the light-receiving fiber 215 of each of the fiber bundles 212a, 213a via an objective optical system (not shown), and received by the photosensor 217, and then the quantity of the reflected light is photoelectrically converted to output a predetermined voltage value.

This voltage value is amplified in a predetermined manner with the amplifying circuit 220, and output to the driving unit 208, and the analog signal is converted to a digital signal with the A/D converter 211 provided in the driving unit 208, and then the digital signal is output to the control unit 222a of the host computer 222.

In the control unit 222a, based on the voltage value corresponding to the quantity of the reflected light detected by the photosensor 217, the presence or absence of scratches, pinholes or distortion on the surface Wf of the disk W is inspected. Namely, when defects such as scratches, pinholes or distortion exist on the surface Wf of the disk W, since the reflected light is scattered, the quantity of the reflected light received by the photosensor 217 is reduced, and the voltage output from the amplifying circuit 220 is also lowered, whereby this disk is judged to be defective. The result of the judgement is displayed on the monitor 222b.

Incidentally, as shown in FIG. 12, when the length of each of the fiber arrays 212, 213 in two lines is set so as to substantially cover at least the recording area in the radius direction of the surface Wf of the disk W, since respective fiber arrays 212, 213 are arranged in a state that the phases thereof are shifted with a half pitch, the presence or absence of defects on the entire recording surface of the surface Wf of the disk W can be inspected only by transferring the photosensor body 205 by a half of the pitch P of the fiber bundles 212a, 213a in a predetermined speed.

Accordingly, in this embodiment, the defects on the surface Wf of the disk W can be inspected only with the quantity of the reflected light detected by the photosensor 217.

As mentioned above, according to this embodiment, since the photosensor body 205 is transferred, the fiber arrays 212, 213 may be constituted by the fiber bundles 212a, 213a arranged with a predetermined pitch P without arranging the fiber bundles 212a, 213a densely, and since the presence or absence of defects can be inspected based on the quantity of the reflected light, arithmetic processing can be made easily and the apparatus can be produced at a low cost in total.

Figure 15:
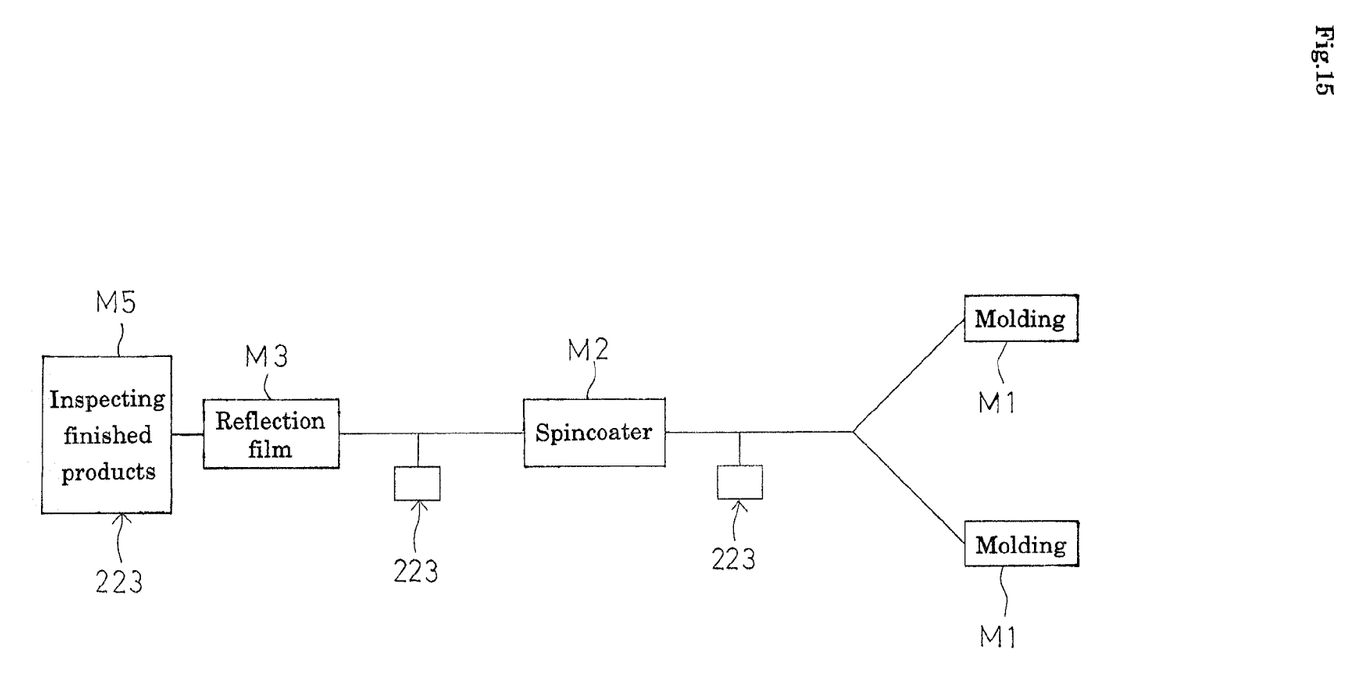
FIG. 15 is an explanatory view showing an application example of this embodiment.

Since the unit cost of product of the disk inspection apparatus is relatively low, in, for example, the production line of CD (compact disk) as shown in FIG. 15, handler units 223 having the disk inspection apparatuses of this embodiment incorporated may be arranged between a step M1 for molding a polycarbonate resin molded substrate and a step M2 for coating a recording film on the surface of the substrate with a spin coater, etc.; between the step M2 and the subsequent step M3 for providing a reflection film on the surface thereof; and in a step M5 for inspecting finished products.

As a result, the presence or absence of defects on the surface Wf of semi-finished disk W can be inspected between respective steps, whereby the yield of products can be improved.

Figure 16:
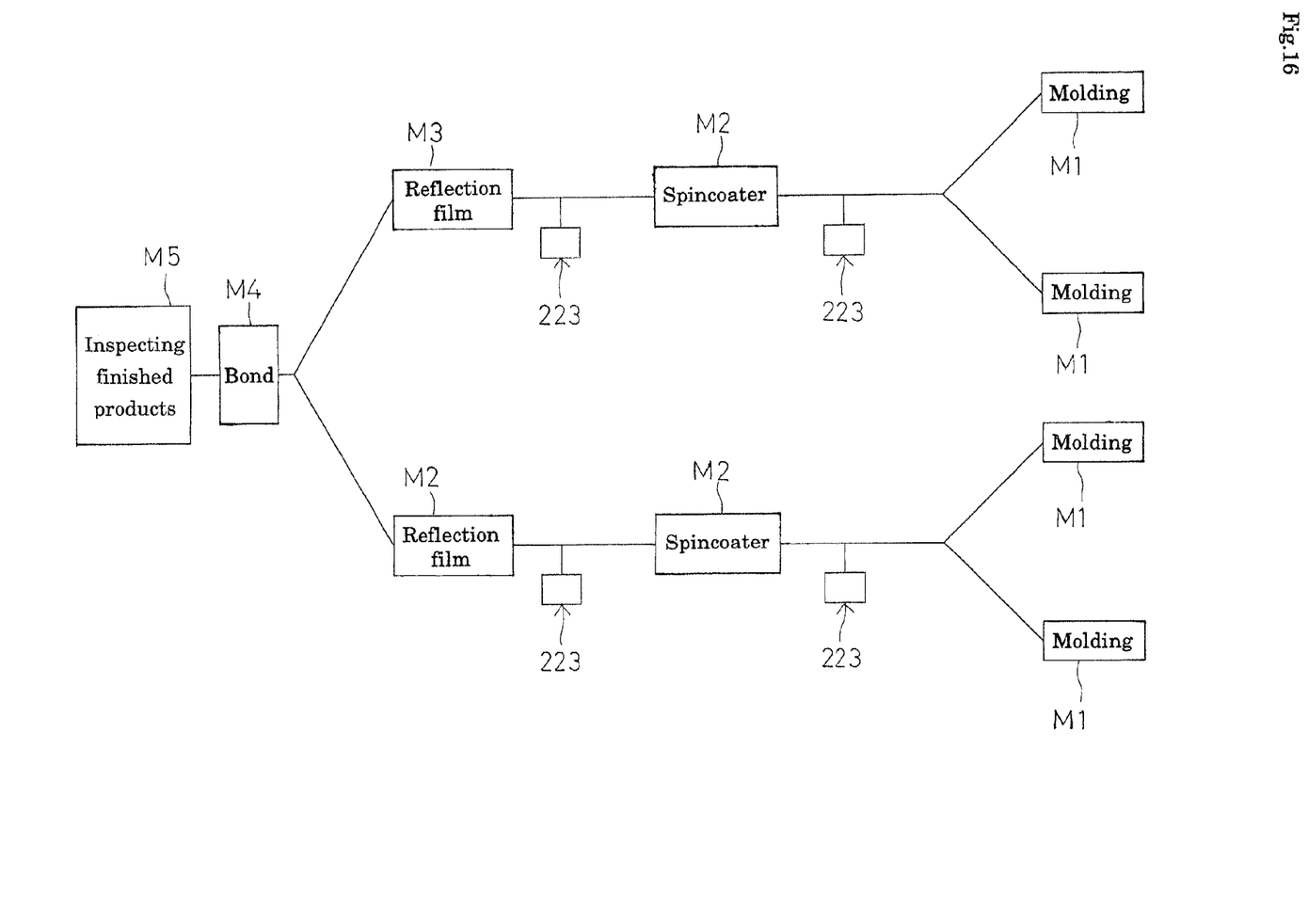
FIG. 16 is an explanatory view showing another application example of this embodiment.

In this case, as shown in FIG. 16, in a production line of, for example, DVD (digital versatile disk) wherein disks W separately produced in the same steps as the production steps of CDs are bonded to each other in the final step M4, the handler units 223 having the disk inspection apparatuses incorporated according to this embodiment may be arranged between respective steps to still further improve the yield of products.

Namely, in a case where inspection is made only on finished products as in a conventional process, even if a disk W in one production line is non-defective, a finished product will be judged to be defective if a disk W in another production line is defective. However, as in this embodiment, by incorporating the inspection apparatuses between respective lines, the defective quality can be detected instantaneously at the step of semi-finished products, whereby the yield of products can be improved.

In this case, respective fiber arrays 212, 213 may be constituted by 9 or more channels, or 7 or smaller channels. Further, the fiber arrays may be constituted by 3 or more lines, and arranged with the phases shifted. Moreover, respective fiber arrays may be arranged radially.

Figure 17:
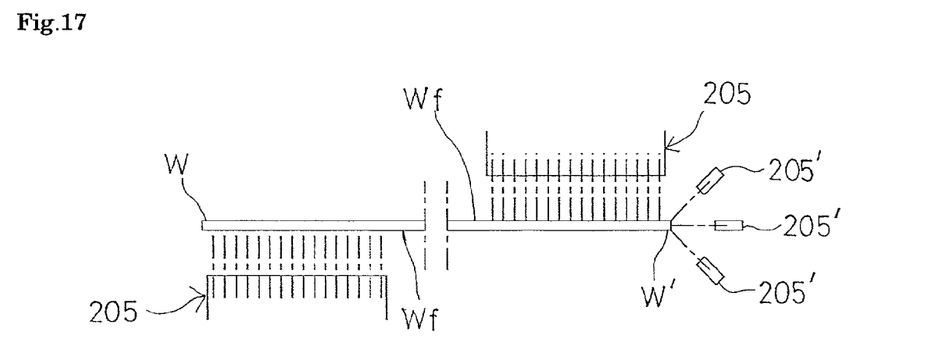
FIG. 17 is a schematic view showing the second embodiment of the disk inspection apparatus.

Next, FIG. 17 shows a schematic view of a disk inspection apparatus according to the second embodiment of the present invention. As shown in this drawing, a magnetic recording disk W constituting a hard disk device (HDD) of a computer is produced by forming a disk-like shape by using a material such as aluminum or glass, and coating its surface with a magnetic material.

Accordingly, in a case of the magnetic recording disk W, photosensor bodies 205 are arranged at both surfaces of the magnetic recording disk W, and in the same operation as in the first embodiment, respective photosensor bodies 205 are reciprocatively moved, during which the presence or absence on the surface of the magnetic recording disk W is inspected.

In this case, by inspecting the edge section W' of the magnetic recording disk W with a single photosensor 205', presence or absence of cracks which are likely to form at edged portions can also be inspected.

As explained above, according to the photosensor device of the present invention, since the light-applying fiber, light-receiving fiber, laser beam source and photosensor are enclosed in one casing, connection with external units with a fiber cable is no longer required, and the durability of the external connection cable can be improved and the reliability of the entire system can also be improved.

Further, according to the disc inspection apparatus of the present invention, since the presence or absence of defects on the disk surface can be inspected using fiber arrays, the unit price of apparatus can be made relatively low, and thus even if a plurality of the apparatuses are arranged in the production steps, the cost for equipment is not substantially affected. In addition, by arranging a plurality of the apparatuses in the production steps, it is possible to detect the defects during the production instantaneously, whereby the yield of products can be improved.

What is claimed is:

1. A disk inspection apparatus for irradiating an inspection light on a surface of a rotating disk and inspecting surface conditions of the disk based on a reflected light, said disk inspection apparatus comprising:
a turning table for rotating the disk;
a photosensor body disposed opposite to the surface of the disk; and
a transfer means for reciprocally transferring the photosensor body in a direction perpendicular to a rotating direction of the disk along the surface of the disk;
wherein the photosensor body comprises a plurality of fiber array, each constructed by arranging a plurality of separate sensor units as multi-channels,
wherein each of the sensor units comprises:
a light-applying fiber,
a light-receiving fiber which is bundled with the light-applying fiber to form a fiber bundle consisting of one light-applying fiber and one light-receiving fiber,
a laser beam source to emit the inspection light to the light-applying fiber,
a photosensor to receive the reflected light via the light-receiving fiber, and
an objective optical system provided at a front end of the fiber bundle, and wherein the sensor units of the fiber arrays are arranged in respective lines such that positional phases of adjacent fiber arrays are shifted with respect to the surface of the disk.

* * * * *